United States Patent
Picou et al.

(10) Patent No.: US 6,524,304 B1
(45) Date of Patent: Feb. 25, 2003

(54) APPARATUS AND METHOD FOR INTRODUCING ONE OR MORE BRANCH LINES INTO IV TUBING

(75) Inventors: Greg Picou, Gulfport, MS (US); Daniel Daigle, Baton Rouge, LA (US); Larry S. Miller, Carencro, LA (US)

(73) Assignee: Scan Corporation, Gulfport, MS (US)

( * ) Notice: Subject to any disclaimer, the term of this patent is extended or adjusted under 35 U.S.C. 154(b) by 0 days.

(21) Appl. No.: 09/689,617

(22) Filed: Oct. 13, 2000

Related U.S. Application Data

(60) Provisional application No. 60/159,433, filed on Oct. 14, 1999.

(51) Int. Cl.[7] ............................................. A61M 39/02
(52) U.S. Cl. ...................... 604/539; 604/534; 604/250
(58) Field of Search ................... 604/500, 264, 604/273, 523, 533, 534, 539, 288.01, 288.02, 288.03, 288.04, 93.01, 175, 250, 6.16, 7; 128/DIG. 6; 264/152; 156/304.2

(56) References Cited

U.S. PATENT DOCUMENTS

RE31,769 E * 12/1984 Hargest et al. ............. 604/500
5,607,391 A * 3/1997 Klinger et al. ............... 604/33
6,298,868 B1 * 10/2001 Dean et al. .................. 137/597

* cited by examiner

Primary Examiner—Brian L. Casler
Assistant Examiner—Mark Han
(74) Attorney, Agent, or Firm—Lowe Hauptman Gilman & Berner, LLP

(57) ABSTRACT

An apparatus for introducing one or more branch fluid lines into IV tubing is disclosed. The apparatus including a pair of first and second fluidic blocks having a pair of contact surfaces that may be arranged to respectively engage each other in sealing contact. At least one cutting member is operatively moveable through, or connected, to the other block. In a two cutting member embodiment, a conduit extends between two cutting members and has opposite open ends in communication with an outer side of the associated cutting member. As the second block contact surface is moved towards the first block contact surface, the cutting members cut a portion of the IV tubing extending between the grooves. As cutting occurs, the cut end of the tubing sealingly engages with an associated open end of the conduit to thereby provide for uninterrupted fluid communication through the IV tubing. facilitate connection of IV extension lines by simply connecting the extension line to the conduit through the fluid port.

23 Claims, 4 Drawing Sheets

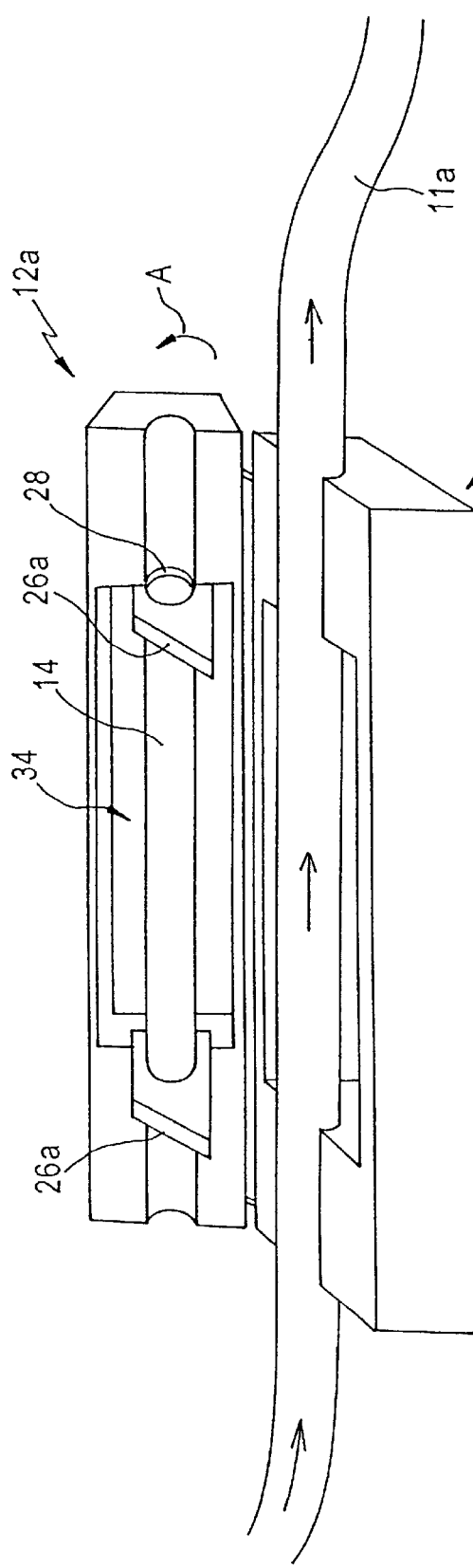
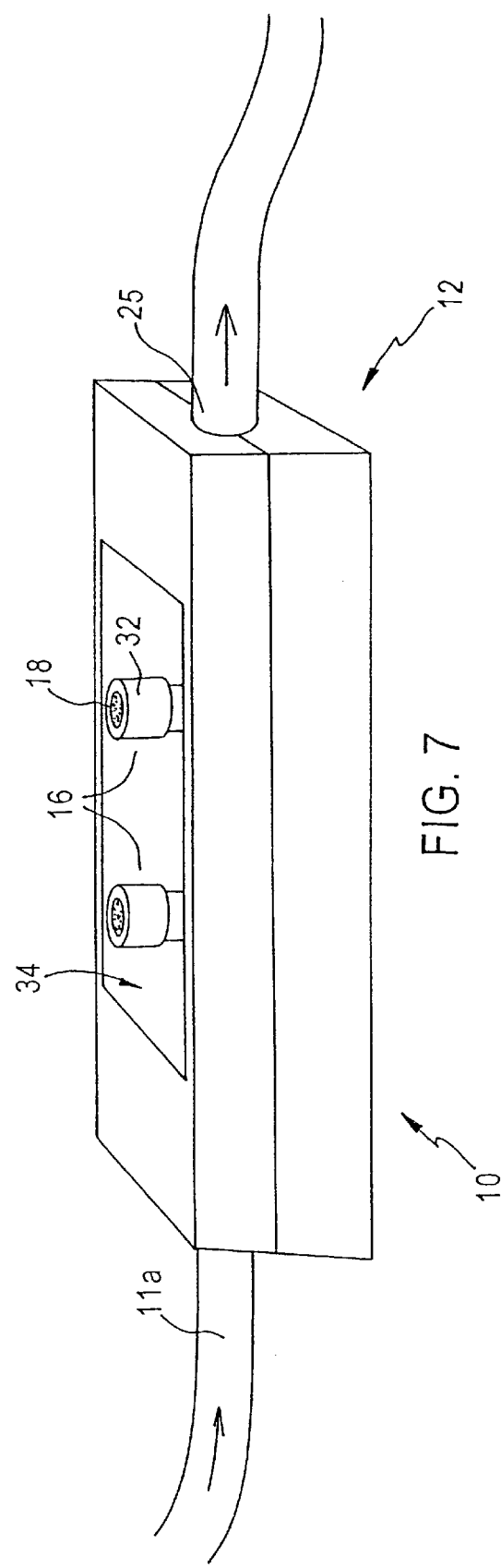
FIG. 6
FIG. 7

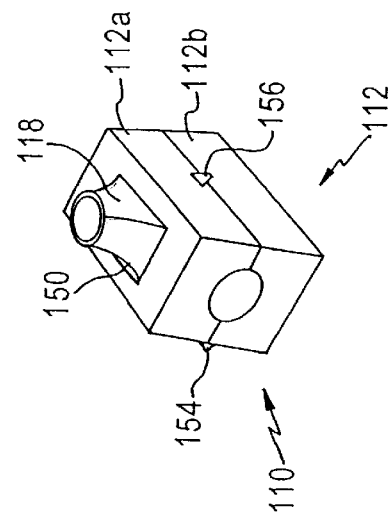
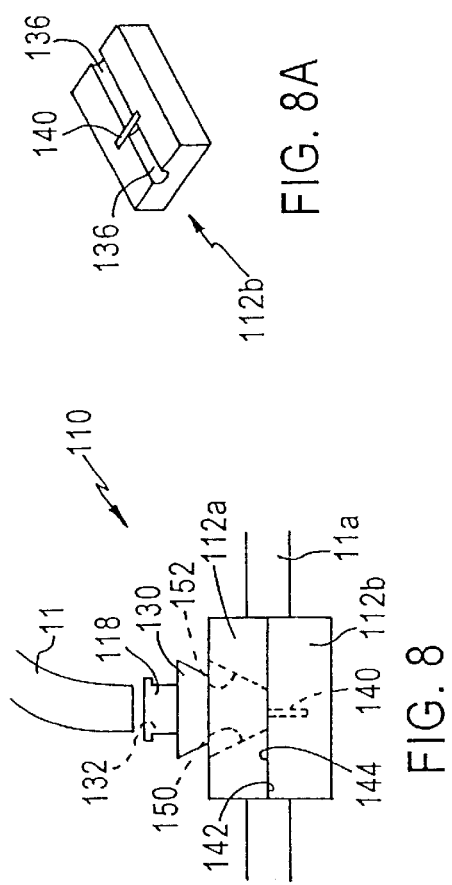
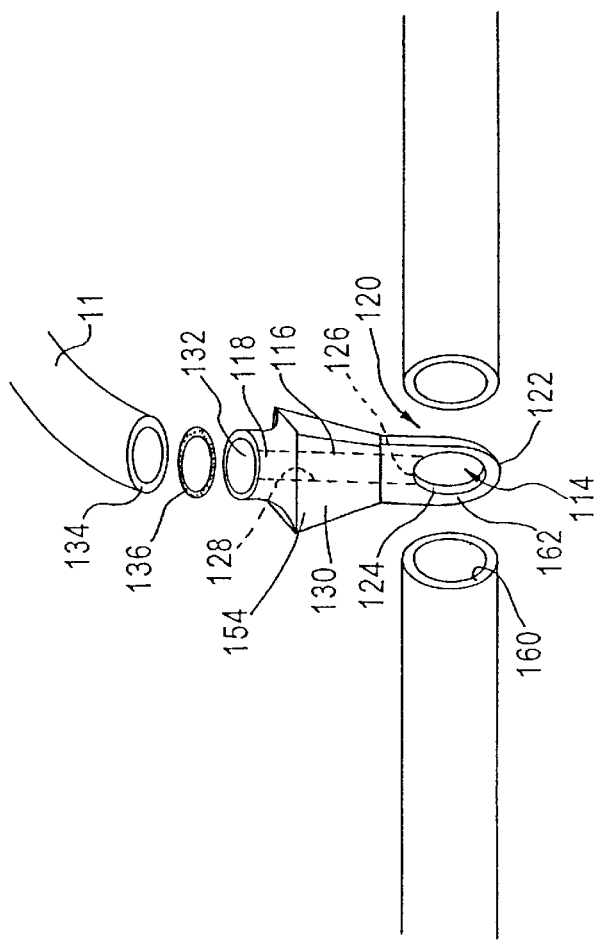

APPARATUS AND METHOD FOR INTRODUCING ONE OR MORE BRANCH LINES INTO IV TUBING

RELATED APPLICATIONS

The present application claims priority of U.S. Provisional Application Ser. No. 60/159,433, filed Oct. 14, 1999, entitled "IV Workshop", the disclosure of which is incorporated by reference herein in its entirety.

TECHNICAL FIELD

The present invention relates generally to the attachment of fluid lines to a main fluid line carrier and, more particularly, to attachment of additional IV fluid lines to a main IV line previously attached to a patient.

BACKGROUND ART

It is not uncommon for a supposedly short surgical procedure to suddenly become a major blood letting ordeal with multiple fluid line requirements. In a number of cases, patients subjected to such procedures were connected to IV tubing that did not contain an IV extension line. Without a break in the IV line, an administering physician or other medical personnel may be unable to place a stopcock to add additional lines to allow for the introduction of warm fluids and special drips. To set up such a system, it is necessary for the administering physician or medical personnel to work their way down to the patient's hand in order to remove the IV tape, place an extension line at a three way stopcock, flush the line out with fluids, and then retape the IV to the patient's hand yet again. This is a long and possibly tedious undertaking, particularly if the patient's arms are adducted and the patient needs blood and close attention.

Other unplanned or emergency situations relate to when a patient suddenly becomes medically stressed and nipride, neosynephrine, or nitroglycerine drips are needed. With these potent medications, it is important to place the drip lines as close as possible to the patient's body. Without an extension line, the foregoing time intensive procedure may be necessary to add a drip line. Even in situations where an extension line already exists, such lines are usually quite some distance from the patient's blood vessels to the newly added stopcock. Medical personnel must at this point run a high fluid rate in order to obtain the desired nitrated levels quickly, and then readjust the fluid rate at a later time.

On the other hand, if the patient is fluid restricted, fluids must be dripped at low rates to prevent dangerous unexpected bolus doses which will waste precious time caring for a failing patient.

Another problem with conventional systems of which I am aware relates to the addition of lines to the IV ports via needles or stopcocks which usually decreases the internal diameter of the fluid line at the exact site of entry. This necessarily slows down fluid rates which is disadvantageous in times of high stress due to blood loss or high fluid requirements.

Another problem occurs if the injection port is located at an inconvenient position requiring the attending medical personnel's body to lean and stretch under sterile drapes each time medications are injected.

It is accordingly an object of the present invention to jointly or severally avoid the prior art problems noted above.

Another object is to easily add one or more fluid extension lines to an existing main IV line already connected to a patient's blood vessels.

Another object is to both quickly and easily add one or more additional IV extension lines to any location along an existing line in relation to an in situ IV catheter.

DISCLOSURE OF THE INVENTION

Apparatus for introducing one or more IV fluid extension lines into a main IV tubing, preferably already connected to a patient's blood vessels, is disclosed. The apparatus comprises a housing with an inlet section and an outlet section spaced from each other and adapted to receive the existing IV main tubing therein. One or more cutting members are respectively mount adjacent the inlet and outlet sections to engage and cut a length of the IV tubing extending between the inlet and outlet sections. In one embodiment, conduit is connected to and extends between the cutting members. The conduit has open opposite ends being arranged to respectively sealingly engage with a cut end of the IV tubing upon cutting of the tubing with an associated one of the cutting members. At least one branch is connected to extend from the conduit in fluid communication therewith. This at least one branch includes a fluid port that may be easily connected to a branch line.

In one embodiment of the invention, the housing includes a pair of first and second fluidic block members, each block member being form with a pair of grooves spaced from each other along a length of the block member. With the block members moved together to a shut position, the grooves in the first and second block members mate with each other to define an inlet passage in the inlet section and an outlet passage in the outlet section. These passages are configured to receive and clampingly engage an outer surface of the IV main tubing received therein in sealing contact therewith.

The first block member further includes the conduit extending between the associated pair of grooves and the pair of cutting members are located at respective opposite ends of the conduit with each open end of the conduit extending through the associated cutting member. The second block includes a cutout formed between the grooves in the inlet and outlet sections. The length of tubing to be cut extends through the cutout prior to cutting. With this arrangement, a cut portion of the IV tubing may pass through the cutout for disposal subsequent to cutting, advantageously replaced by the conduit which moves into fluid communication position as the cutting member sliced through the IV tubing portion to be discarded.

In one embodiment, the first and second blocks are pivotally secured together for movement between the open and shut positions.

In other embodiments, a plurality of branch lines may be formed along the conduit, each branch line containing a separate fluid port easily connected to an extension fluid line as needed. With this arrangement, it is also possible to provide fluid ports of different diameter to accommodate the diverse types of solutions that may be needed during different procedures.

A method of facilitating the introduction of one or more fluid lines into an IV tubing preferably previously connected to a patient is also disclosed. The method comprises the steps of laying a portion of the IV tubing into a pair of grooves formed in a first member. The IV tubing portions in the grooves are then clamped with a second member. The IV tubing between the grooves is then cut at a location respectively adjacent the grooves. As this cutting occurs, a continuous fluid path through the IV tubing is provided by replacing the cut portion of the IV tubing with a conduit having opposite ends in respective sealing contact and fluid communication with the associated cut ends of the tubing. The conduit is formed with a fluid port that may be accessed by an external line.

The method of the invention comprises a further step of attaching such an additional branch line to the IV tubing by connecting the line to the fluid port.

With the foregoing apparatus and method of the present invention, it will be appreciated that the first member is positionable at infinitely variable locations along the in situ IV tubing. In this manner, if medicaments requiring immediate entry into a patient blood vessels is necessary, the first member may be attached to the main IV line at a location immediately adjacent the IV line catheter.

It is within the scope of this invention to provide an apparatus and method that utilizes a single cutting member in place of the pair of cutting members discussed herein above. This single cutting member is preferably formed with a through hole having the same innerdiameter as the innerdiameter of the main IV tubing being cut. Opposite sides of the cutting member defining the through hole opening are capable of sealingly engaging with the cut areas of the IV tubing upon cutting of the same with the single cutting member. In other words, the conduit is replaced with the through hole. Both the through hole and the cutting edge are preferably formed in a spade member that is hollow to receive a branch IV line enabling fluid flow through the hollow area into the through opening.

The above and still further objects, features and advantages of the present invention will become apparent upon consideration of the following detailed description of a specific embodiment thereof, especially when taken in conjunction with the accompanying drawings.

BRIEF DESCRIPTION OF THE DRAWING

FIG. 6 is a perspective view similar to FIG. 4, depicting the main IV tubing received between the block members in their open positions;

FIG. 7 is a perspective view depicting the block members in their closed or shut position;

FIG. 8 is a side view of a preferred embodiment of the present invention;

FIG. 9 is an exploded perspective view depicting various components of the preferred embodiments; and FIG. 10 is a perspective view of the preferred embodiment of the invention unattached to main IV tubing.

BEST MODE FOR CARRYING OUT THE INVENTION

Figure 5:
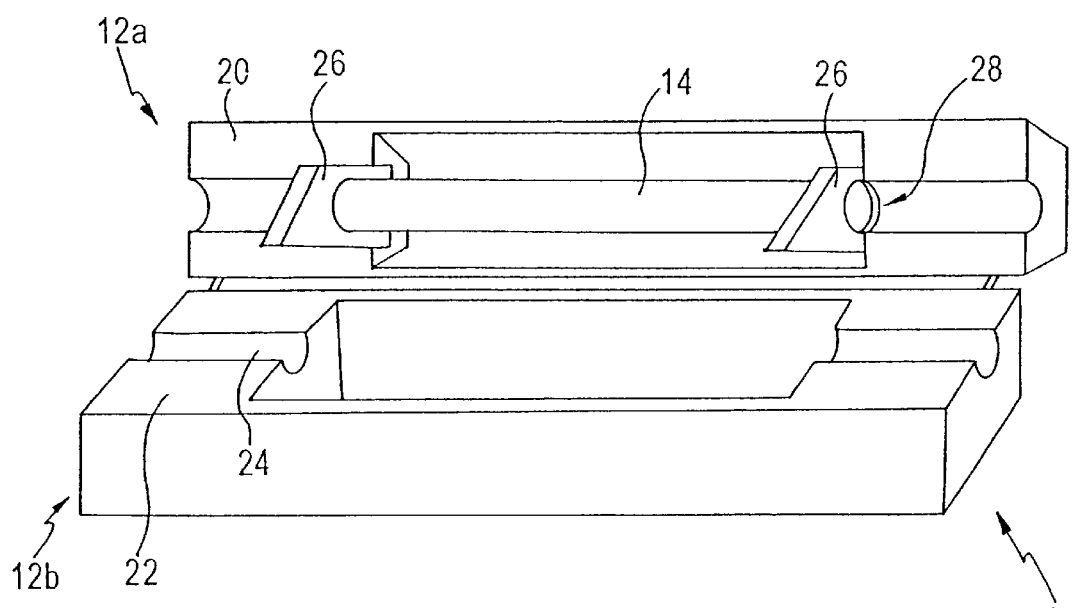
FIG. 5 is a perspective view depicting the upper and lower block housings in an open position relative to each other in order to receive a portion of a main IV tubing.

FIGS. 5 and 10 are perspective view illustrations of two embodiments 10 and 100, respectively, for introducing one or more IV extension lines 11 into a main IV tubing 11a that may or may not already be secured to a patient's blood vessels via a conventional catheter (not shown in detail). Common to each embodiment of apparatus 10 or 100 is a fluidic block 12 or 112 respectively, each formed into two sections 12a and 12b or 112a or 112b, that may be opened to receive a portion of the main IV tubing 11a such as depicted in FIG. 6.

Figure 1:
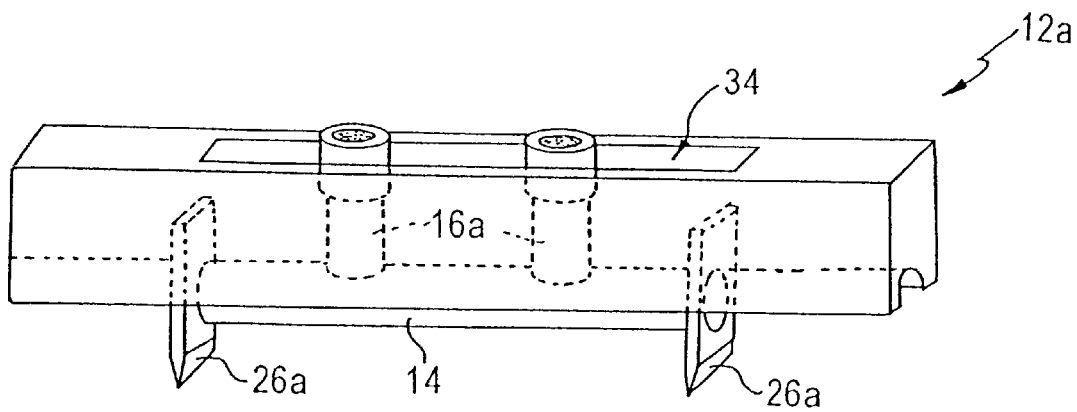
FIG. 1 is a perspective view of an upper fluidic block with a cutting blade and a conduit configuration in accordance with one embodiment of the invention.
Figure 2:
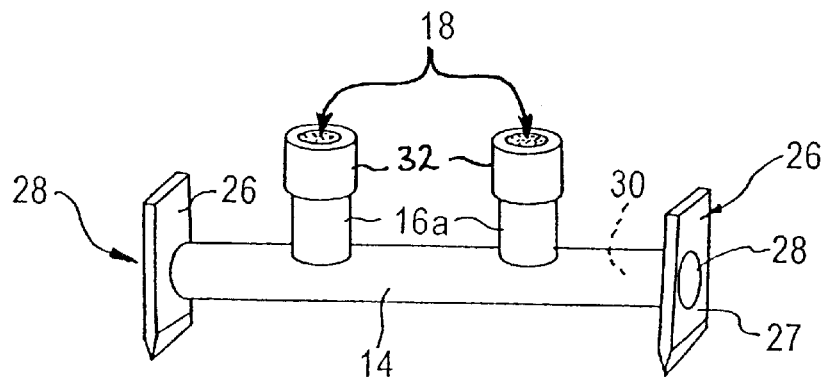
FIG. 2 is a perspective view illustration of the cutting blade and conduit configuration in detach condition from the upper block housing in accordance with the FIG. 1 embodiment.
Figure 3:
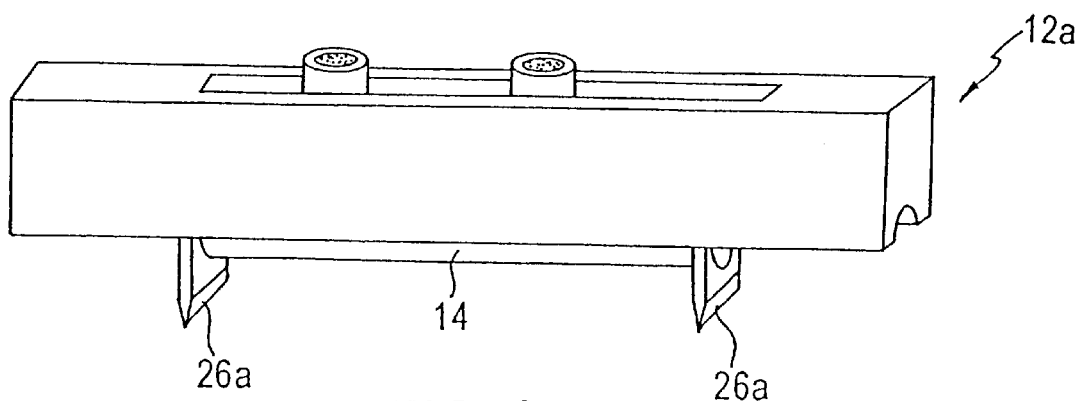
FIG. 3 is a perspective view similar to FIG. 1 depicting the upper block housing components in assembled condition.
Figure 4:
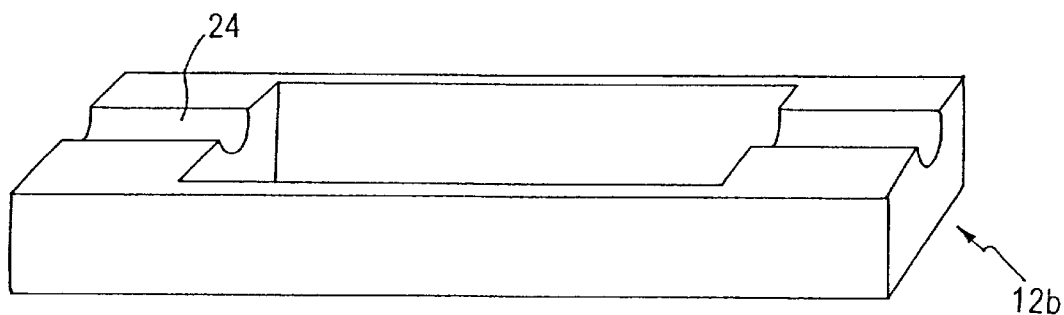
FIG. 4 is a perspective view of a bottom block housing used in conjunction with the upper block housing of FIG. 1.

One of the fluidic block sections 12a or 112a is formed to receive one or more cutting edges, described in detail below, that gradually cuts through the main IV tubing 11a as the blocks 11a, 12a, 12b or 112a, 112b are closed together. As the cutting action occurs, the severed portion of IV tubing is replaced with a rigid conduit 14 (FIG. 2) or a through opening (FIG. 9) each formed with a branch member 16 or 116, respectively, in fluid communication therewith. This branch member 16 or 116 is in turn formed with a fluid port 18, 118 that may be easily connected to an IV extension line 11. Either embodiment is advantageously constructed to be rapidly and easily connected to main IV tubing 11a at any point along the main IV line between the catheter and fluid source to provide for immediate or sudden intervention of an extension line with other types of medicaments.

Referring now to the first embodiment depicted in FIGS. 1–7 of the drawing, apparatus 10 is comprised of the pair of upper and lower fluidic block members 12a and 12b. In the open position depicted in FIG. 5, it can be seen that upper block member 12a has a downwardly directed surface 20 adapted to sealingly engage with an upwardly directed surface 22 of the lower block member 12b. Both the upper and lower blocks 12a, 12b are preferably formed with grooves 24 that define an inner diameter, in the closed or shut position (FIG. 7), that clampingly and sealingly engages an outer surface 25 of the IV tubing 11a. Preferably, each of the grooves 24 in the inlet section of the fluidic blocks 12a, 12b are semi cylindrical in cross section to define a cylindrical inlet passage receiving the section of IV tubing 1a extending from a fluid source.

The right hand section of each block surface 20, 22 is also formed with semi cylindrical outlet grooves 24 adapted to clampingly and sealingly engage an outer surface of downstream section of the IV tubing 11a located between the inlet section and the IV catheter (not shown).

The upper block housing 12a includes the cylindrical conduit 24 and a pair of cutting members 26 are respectively formed at opposite ends 28 thereof with downwardly direct cutting blades 26a. Each opposite end 28 of the conduit 14 is open to the outer vertical side 27 of the associated cutting member 27. One or more of branches 16 project orthogonally from the conduit 14 at longitudinally spaced intervals from each other. Each branch 16 has a passageway 16a in fluid communication with the through passage 30 formed in the conduit 14. An outwardly directed upper end 32 of the branch 16 is formed with fluid port 18 that is normally sealed shut but may be easily pierced or otherwise opened upon insertion of an IV extension line 11 therein.

A central cavity 34 extending through the upper block housing 12a is configured to receive the conduit/cutting blade assembly 14, 26 therein so that the cutting blades 26 are in respective alignment with the innermost end of an associated one of the grooves 24 as best depicted in FIG. 5. In this condition, best depicted in FIGS. 1 and 3, the IV branches 16 project outwardly from the upper block 12a through the cutout for easy access or insertion of an IV extension line 11 through the fluid port 18.

In use, the IV main tubing 11a is initially disposed in the longitudinally space lower grooves 24 as best depicted in FIG. 6. The upper block 12a is then pivoted from the open position of FIG. 6 to the closed position of FIG. 7 about arrow. As the cutting blades 26a contact and begin to cut the tubing 11a at the innermost ends of the grooves 24, it will be appreciated that the open ends 28 of the conduit 14 begin to enter into sealing contact with the freshly cut tubing edges in both the inlet and outlet sections. Upon completion of cutting, the open ends 28 of the conduit 14 are in respective sealing contact with the associated freshly cut tubing end to provide leak proof continues flow through the IV tubing main line 11a without fluid restriction.

It will be appreciated that the foregoing apparatus 10 can be quickly and easily clamped to any portion of IV main tubing 11a. Once so clamped, one or more additional extension lines 11 can be added to the main line 11a by easy insertion of the extension line into the fluid extension port 18.

FIGS. 8–10 are illustrations of a second or preferred embodiment of this invention in which the apparatus 110 is formed with a single spade like member 120 having a sharp cutting edge 122 formed in the rounded distal end thereof The conduit 14 of the first embodiment is actually defined by a cylindrical side wall 124 of through hole extending through the spade like member 120 and a portion 126 of this through hole 114 is opened to a passageway 128 formed in an extension part 130 of the spade like member having an opposite open end 132 adapted to receive an end 134 of IV extension tubing 11 attached thereto, with or without the inter positioning of an -o-ring-136.

One advantage of apparatus 110 of the preferred embodiment is that only a single cut is made in the main IV tubing 11a to introduce a branch line 11 anywhere along the main line 11a. This enables apparatus 110 to be of a more compact configuration than apparatus 10 and also eliminates a need for severing and wasting a length of the IV main tubing as defined between the cutting members 26. In the preferred embodiment, the lower block 112b is formed with a pair of grooves 136 that are separated from each other at inner ends thereof only by a slit 140 of sufficient width to receive the spade like cutting member 122 into the assembly when the upper block 112a is pivoted into closed or shut position with the lower block 126 as depicted in FIGS. 8–10. The facing surfaces 142, 144 in which the upper and lower grooves 136 are formed in the respective blocks 112a, 112b are designed to clamp and seal against each other as in the first embodiment. The knife receiving slit 140 formed in the lower block 112b need not extend completely through the block thickness since no waste of IV tubing 11a occurs with this embodiment.

The upper block 112a is formed with a central cavity 150 (see FIG. 8) extending through the thickness of the upper block so that cavity walls 152 thereof are in sealing contact with surfaces or sidewalls 154 of the extension member 130 projecting upwardly from the spade like member 120.

In other words, once the uncut tubing is disposed in the grooves 136 of the lower block 112b, the hinged upper block 112a in the open position is pivoted about hinge 154 into a closed position and then latched at 156 as shown in FIG. 10. At this point, the spade like cutting member 120 is inserted into the upper block cavity 150 through an upper end thereof to gradually descend into cutting contact with the tube 11a spanning the receiving slit 140 in the lower block coaxial. Once cut, the through opening 114 in the spade like member 120 is in coaxial alignment with the cut ends of the severed IV main line 11a and the resulting cut ends 160 enter into liquid sealing engagement with the side surfaces 162 of the spade like member 126 respectively surrounding the through opening. In this manner, unrestricted flow throughput is achieved through the extension 130. advantageously enabling a branch IV line 11 to be attached to the extension part to provide an adequate supply of auxiliary fluid where needed.

It will be evident that there are additional embodiments which are not illustrated above but which are clearly within the scope and spirit of the present invention. For example, it is within the scope of this invention to mount a floss cutter in the form of a metal tongue (not shown) to the housing of any of the above and additional embodiments to cut any extraneous ends or undesirable floss lengths from the floss circuit. The above description and drawings are therefor intended to be exemplary only in nature and the scope of the invention is to be limited solely by the appended claims.

What is claimed is:

1. Apparatus for introducing one or more fluid ports into IV tubing, said apparatus comprising:

a housing with an inlet section and an outlet section spaced from each other and adapted to receive said IV tubing therein;

a pair of cutting members respectively mounted adjacent the inlet and outlet sections to engage and cut a length of said IV tubing extending between said inlet and outlet sections;

a conduit connected to and extending between said cutting members, said conduit having opposite open ends each being arranged to respectively sealingly engage with a cut end of the IV tubing upon cutting of the same with an associated one of said cutting members; and at least one branch connected to extending from said conduit in fluid communication therewith and including a fluid port.

2. The apparatus of claim 1, wherein said housing includes a pair of first and second block members, each block member being formed with a pair of grooves spaced from each other along a length of the block member, and wherein, with said block members moved into a shut position, the grooves in said first and second block members mate with each other to define an inlet passage in the inlet section and an outlet passage in the outlet section.

3. The apparatus of claim 2, wherein the inlet and outlet passages are structured to receive and clampingly engage an outer surface of the IV tubing received therein in fluid sealing contact therewith.

4. The apparatus of claim 3, wherein said first block member further includes said conduit extending between the pair of grooves and said pair of cutting members are located at respective opposite ends of said conduit with each of the open ends of said conduit extending through said cutting member.

5. The apparatus of claim 4, wherein said second block includes a cutout formed between said grooves, said length of tubing to be cut extending through said cutout prior to cutting.

6. The apparatus of claim 4, wherein said first block is formed with a cutout through which said at least one branch extends to permit external access to said fluid port.

7. The apparatus of claim 4, wherein said first and second blocks are pivotally secured together for movement between open and shut positions.

8. The apparatus of claim 1, further comprising a plurality of said fluid ports formed along the conduit at spaced intervals from each other.

9. The apparatus of claim 8, wherein said ports have different diameters from each other.

10. The apparatus of claim 1, wherein said housing, said conduit, and said at least one branch are formed of plastic.

11. The apparatus of claim 10, wherein said cutting members are formed from at least one of plastic and metal.

12. Apparatus for introducing a fluid port into IV tubing, said apparatus comprising
- a housing formed with an inlet section and an outlet section spaced from each other and being adapted to receive said IV tubing therein,
- a cutting member being insertable through an opening formed in said housing to engage and cut said IV tubing;
- a through opening formed in said cutting member, said through opening being defined by opposing surfaces located respectively on opposite sides of the cutting member to respectively sealingly engage with an associated cut end of the IV tubing upon cutting of the IV tubing with said cutting member; and
- at least one branch connected to extending from said cutting member in fluid communication with said through opening.

13. A method of facilitating the introduction of one or more fluid lines into an IV tubing connected to a patient, said method comprising the steps of:
- a. laying a portion of said IV tubing in a pair of grooves formed in a first member;
- b. clamping said IV tubing portion in said grooves with a second member;
- c. cutting said IV tubing by a cutting member at least one location respectively adjacent to the grooves; and
- d. providing a continuous fluid path through the IV tubing by replacing the cut portion of the IV tubing with a through opening in said cutting member having opposite ends in respective sealing contact and fluid communication with associated cut ends of the IV tubing.

14. The method of claim 13, comprising the further step of attaching a branch line to said IV tubing by connecting the branch line to a fluid port, communicating with said through opening.

15. The method of claim 14, wherein said through opening extends through a conduit formed with a plurality of fluid ports, and comprising the further step of attaching a multitude of branch lines to respective ones of said fluid ports.

16. The method of claim 15, wherein said first member is positionable at infinitely variable locations along the IV tubing.

17. The method of claim 15, wherein said conduit is formed in said second member having a pair of said cutting members respectively positioned at opposite ends of said conduit, and wherein steps (b), (c) and (d) of claim 13 simultaneously occur by moving said second member into operative engagement with the first member.

18. The method of claim 17, wherein said first and second members are hinged together and move into contact about a hinge access.

19. A method of facilitating the introduction of one or more fluid lines into an IV tubing, said method comprising the steps of:
- a. cutting said IV tubing, by a cutting member, at at least one cutting location; and
- b. providing a continuous fluid path through the IV tubing and a through opening in the cutting member, said through opening having opposite ends in respective sealing contact and fluid communication with associated cut ends of the IV tubing.

20. The method of claim 19, wherein steps (a) and (b) simultaneously occur by moving the cutting member to cut the IV tubing.

21. The method of claim 20, further comprising supporting the IV tubing at two supporting locations on opposite sides of said at least one cutting location prior to said cutting.

22. The method of claim 21, further comprising the step of clamping the IV tubing at the supporting locations simultaneously with steps a) and b).

23. The method of claim 20, wherein step a) comprises cutting the IV tubing at two said cutting locations, and step b) comprises replacing a cut portion of the IV tubing with a conduit extending between said two cutting locations and defining said through opening.

* * * * *